(12) United States Patent
Li

(10) Patent No.: US 9,597,049 B2
(45) Date of Patent: Mar. 21, 2017

(54) IMAGE DISPLAY CONTROL DEVICE, OPERATING METHOD FOR SAME, AND IMAGE DISPLAY CONTROL PROGRAM

(71) Applicant: FUJIFILM Corporation, Tokyo (JP)

(72) Inventor: Yuanzhong Li, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/079,697

(22) Filed: Mar. 24, 2016

(65) Prior Publication Data

US 2016/0199015 A1 Jul. 14, 2016

Related U.S. Application Data

(63) Continuation of application No. PCT/JP2014/004954, filed on Sep. 26, 2014.

(30) Foreign Application Priority Data

Sep. 30, 2013 (JP) .................................. 2013-203027

(51) Int. Cl.
*H04N 13/04* (2006.01)
*A61B 6/00* (2006.01)
(Continued)

(52) U.S. Cl.
CPC .............. *A61B 6/463* (2013.01); *A61B 5/744* (2013.01); *A61B 5/7425* (2013.01);
(Continued)

(58) Field of Classification Search
CPC ....... A61B 6/466; A61B 6/463; A61B 5/7435; A61B 5/744; A61B 6/032; A61B 5/7425; H04N 13/0497
(Continued)

(56) References Cited

U.S. PATENT DOCUMENTS

2007/0118408 A1 5/2007 Mahesh et al.
2008/0212854 A1 9/2008 Fukatsu et al.
(Continued)

FOREIGN PATENT DOCUMENTS

JP H 11-290279 A 10/1999
JP 2001-120541 A 5/2001
(Continued)

OTHER PUBLICATIONS

German Office Action dated Jun. 6, 2016 with an English translation thereof.
(Continued)

*Primary Examiner* — Jamie Atala
*Assistant Examiner* — Nguyen Truong
(74) *Attorney, Agent, or Firm* — McGinn IP Law Group, PLLC

(57) ABSTRACT

The image display control device includes a thumbnail image display control unit that displays a thumbnail image of a tomographic image forming a three-dimensional image, a display instruction receiving unit that receives an instruction to display the three-dimensional image, and a tomographic image display control unit that displays a plurality of tomographic images on a display screen which is different from a display screen on which the thumbnail image is displayed such that the tomographic images are sequentially switchable when the instruction to display the three-dimensional image is received. The thumbnail image display control unit newly generates a thumbnail image of the tomographic image displayed immediately before the display of the tomographic image ends, changes the current thumbnail image to the new thumbnail image, and displays the new thumbnail image.

12 Claims, 12 Drawing Sheets

(51) Int. Cl.
  *G06Q 50/24* (2012.01)
  *A61B 6/03* (2006.01)
  *A61B 5/00* (2006.01)
(52) U.S. Cl.
  CPC ............ *A61B 5/7435* (2013.01); *A61B 6/032* (2013.01); *G06Q 50/24* (2013.01); *H04N 13/0497* (2013.01); *A61B 6/466* (2013.01)
(58) Field of Classification Search
  USPC .......................................................... 348/51
  See application file for complete search history.

(56) References Cited

U.S. PATENT DOCUMENTS

2009/0132274 A1   5/2009   Mahesh et al.
2013/0187903 A1   7/2013   Papageorgiou et al.

FOREIGN PATENT DOCUMENTS

| JP | 2002-253545 A | 9/2002 |
| JP | 2005-270328 A | 10/2005 |
| JP | 2007-144179 A | 6/2007 |
| JP | 2008-200085 A | 9/2008 |
| JP | 2008-200139 A | 9/2008 |
| JP | 2008-264167 A | 11/2008 |
| JP | 2011-120827 A | 6/2011 |

OTHER PUBLICATIONS

Johnson, Hans J.; Christensen, Gary E., "Consistent landmark and intensity-based image registration", IEEE Transactions on Medical Imaging, May 2002, vol. 21. Jg., No. 5, pp. 450-461.

International Search Report (ISR) (PCT Form PCT/ISA/210), in PCT/JP2014/004954, dated Jan. 20, 2015.

International Search Opinion (PCT/ISA/237) in PCT/JP2014/004954 and an English translation thereof, dated Jan. 20, 2015.

Oyama Kazuo, ""NEXTAS"Clinical Information Integration and Management System", Yokogawa Technical Report, vol. 48, No. 4 (2004), pp. 125-128 and a translation thereof.

German Office Action dated Jan. 19, 2016 with an English translation thereof.

Wikipedia, "Bildregistrierung", https://web.archive.org/web/20130203043311/http://de.wikipedia.org/wiki/Bildregistrierung Feb. 3, 2013.

FIG. 5

| FEBRUARY 20 REPORT 1 CT1 | | MARCH 10 ENDOSCOPE DOCTOR'S OPINION |
|---|---|---|
| | MAY 8 REPORT 2 CT2 | |
| OCTOBER 12 REPORT 3 BLOOD TEST CT3 | | |

W1

| TOMOGRAPHIC IMAGE OF CT1 | TOMOGRAPHIC IMAGE OF CT2 | TOMOGRAPHIC IMAGE OF CT3 |
|---|---|---|

W2

IMAGE DISPLAY CONTROL DEVICE, OPERATING METHOD FOR SAME, AND IMAGE DISPLAY CONTROL PROGRAM

CROSS-REFERENCE TO RELATED APPLICATIONS

This application is a Continuation of PCT International Application No. PCT/JP2014/004954 filed on Sep. 26, 2014, which claims priority under 35 U.S.C. §119(a) to Japanese Patent Application No. 2013-203027 filed on Sep. 30, 2013. Each of the above applications is hereby expressly incorporated by reference, in its entirety, into the present application.

BACKGROUND OF THE INVENTION

1. Field of the Invention

The present invention relates to an image display control device that displays a thumbnail image of a tomographic image forming a three-dimensional image and displays a plurality of tomographic images forming the three-dimensional image such that the tomographic images are sequentially switchable when an instruction to display the three-dimensional image is received, a method for operating the image display control device, and an image display control program.

2. Description of the Related Art

In recent years, a medical examination information integration system which enables a user to view various examination images of patients or radiograph interpretation reports has come into widespread use (for example, see Oyama Kazuo, "Clinical Information Integration and Management System NEXTAS", Yokogawa Technical Report, Vol. 48, No. 4 (2004), pp 125-128).

In the medical examination information integration system, in many cases, when the user clicks a thumbnail image, such as a computed tomography (CT) image which is displayed on a screen of the system, a viewer application starts and a CT image corresponding to the thumbnail image is displayed.

SUMMARY OF THE INVENTION

The thumbnail image which is displayed on the screen of the system is used to roughly check the part of which the CT image is to be captured. Therefore, the system does not particularly consider which of a plurality of tomographic images forming the CT image is used to generate the thumbnail image. For example, a tomographic image in a tomographic plane that is located at the end is used as the tomographic image used to generate the thumbnail image and is fixed.

JP2007-144179A discloses a technique which receives a selected cross section on a three-dimensional image of which the thumbnail image is displayed and displays the selected image, but does not disclose a technique which displays the thumbnail image of one of a plurality of tomographic images forming a three-dimensional image as described above.

JP2002-253545A discloses a technique which displays a plurality of tomographic images in a cine mode and JP2001-120541A does not disclose the technique which displays the thumbnail image of one of a plurality of tomographic images forming a three-dimensional image as described above.

JP2001-120541A and JP2011-120827A disclose a technique which performs a comparative radiograph interpretation between a plurality of tomographic images and do not disclose a technique which displays a thumbnail image.

The invention has been made in view of the above-mentioned problems and an object of the invention is to provide an image display control device, an image display control method, and an image display control program which enable a user to roughly check the part to be captured when the user observes a thumbnail image of a tomographic image and to check previous radiograph interpretation information.

According to an aspect of the invention, there is provided an image display control device including: a thumbnail image display control unit that displays a thumbnail image of a tomographic image forming a three-dimensional image including a plurality of tomographic images; a display instruction receiving unit that receives an instruction to display the three-dimensional image; and a tomographic image display control unit that displays the plurality of tomographic images forming the three-dimensional image on a display screen which is different from a display screen on which the thumbnail image is displayed such that the tomographic images are sequentially switchable, when the display instruction receiving unit receives the instruction to display the three-dimensional image. The thumbnail image display control unit newly generates a thumbnail image of the tomographic image displayed by the tomographic image display control unit immediately before the display of the tomographic image ends, changes the thumbnail image that is currently being displayed to the newly generated thumbnail image, and displays the newly generated thumbnail image.

In the image display control device according to the above-mentioned aspect of the invention, the display instruction receiving unit may receive an instruction to display a plurality of three-dimensional images to be displayed among a plurality of three-dimensional images. When the display instruction receiving unit receives the instruction to display the plurality of three-dimensional images to be displayed, the tomographic image display control unit may display tomographic images of the plurality of three-dimensional images to be displayed side by side.

The tomographic image display control unit may switch the plurality of tomographic images displayed side by side in operative association with each other such that a plurality of tomographic images located in the same tomographic plane are displayed side by side, and display the plurality of tomographic images.

The tomographic image display control unit may switch the plurality of tomographic images in operative association with each other, on the basis of a landmark which is detected in advance from each of the plurality of three-dimensional images to be displayed, and display the plurality of tomographic images.

When the plurality of three-dimensional images to be displayed have different imaging directions, the tomographic image display control unit may generate tomographic images having the same imaging direction, and display the tomographic images.

The image display control device according to the above-mentioned aspect of the invention may further include a tomographic plane position change instruction receiving unit that receives an instruction to change the position of a tomographic plane of a tomographic image to be displayed among the plurality of tomographic images forming the three-dimensional image. The tomographic image display control unit may display the tomographic image at the position of the tomographic plane changed by the tomographic plane position change instruction receiving unit.

The image display control device according to the above-mentioned aspect of the invention may further include a tomographic plane position display control unit that displays an image indicating the position of a tomographic plane of the thumbnail image, which is currently being displayed, on a display screen on which the thumbnail image is displayed.

The tomographic plane position display control unit may display the image indicating the position of the tomographic plane on a body icon.

The image display control device according to the above-mentioned aspect of the invention may further include an imaging range display control unit that displays an image indicating an imaging range of a three-dimensional image including the thumbnail image, which is currently being displayed, on the display screen on which the thumbnail image is displayed.

The imaging range display control unit may display the image indicating the imaging range on the body icon.

According to another aspect of the invention, there is provided a method for operating an image display control device including a thumbnail image display control unit, a display instruction receiving unit, and a tomographic image display control unit. The method includes: allowing the thumbnail image display control unit to display a thumbnail image of a tomographic image forming a three-dimensional image including a plurality of tomographic images; allowing the display instruction receiving unit to receive an instruction to display the three-dimensional image; allowing the tomographic image display control unit to display the plurality of tomographic images forming the three-dimensional image on a display screen which is different from a display screen on which the thumbnail image is displayed such that the tomographic images are sequentially switchable, when the instruction to display the three-dimensional image is received; and allowing the thumbnail image display control unit to newly generate a thumbnail image of the tomographic image displayed immediately before the display of the tomographic image ends, to change the thumbnail image that is currently being displayed to the newly generated thumbnail image, and to display the newly generated thumbnail image.

According to another aspect of the invention, there is provided an image display control program that causes a computer to function as: a thumbnail image display control unit that displays a thumbnail image of a tomographic image forming a three-dimensional image including a plurality of tomographic images; a display instruction receiving unit that receives an instruction to display the three-dimensional image; and a tomographic image display control unit that displays the plurality of tomographic images forming the three-dimensional image on a display screen which is different from a display screen on which the thumbnail image is displayed such that the tomographic images are sequentially switchable, when the display instruction receiving unit receives the instruction to display the three-dimensional image. The thumbnail image display control unit newly generates a thumbnail image of the tomographic image displayed by the tomographic image display control unit immediately before the display of the tomographic image ends, changes the thumbnail image that is currently being displayed to the newly generated thumbnail image, and displays the newly generated thumbnail image According to the image display control device, the method for operating the image display control device, and the image display control program of the invention, the thumbnail image of the tomographic image forming the three-dimensional image is displayed. When the instruction to display the three-dimensional image is received, a plurality of tomographic images forming the three-dimensional image are displayed on a display screen which is different from the display screen on which the thumbnail images thereof are displayed such that the tomographic images are sequentially switchable. In this case, when the display of the tomographic image ends, a thumbnail image of the tomographic image displayed immediately before the display of the tomographic image ends is newly generated and the thumbnail image that is currently being displayed is changed to the newly generated thumbnail image. Then, the newly generated thumbnail image is displayed. When observing the changed and displayed thumbnail image, the user can instantaneously check which of the tomographic images has been mainly observed in the previous radiograph interpretation. Therefore, it is possible to improve the efficiency of diagnosis.

BRIEF DESCRIPTION OF THE DRAWINGS

FIG. 5 is a diagram illustrating a case in which a plurality of three-dimensional images are selected and a plurality of tomographic images are displayed side by side.

DESCRIPTION OF THE PREFERRED EMBODIMENTS

Figure 1:
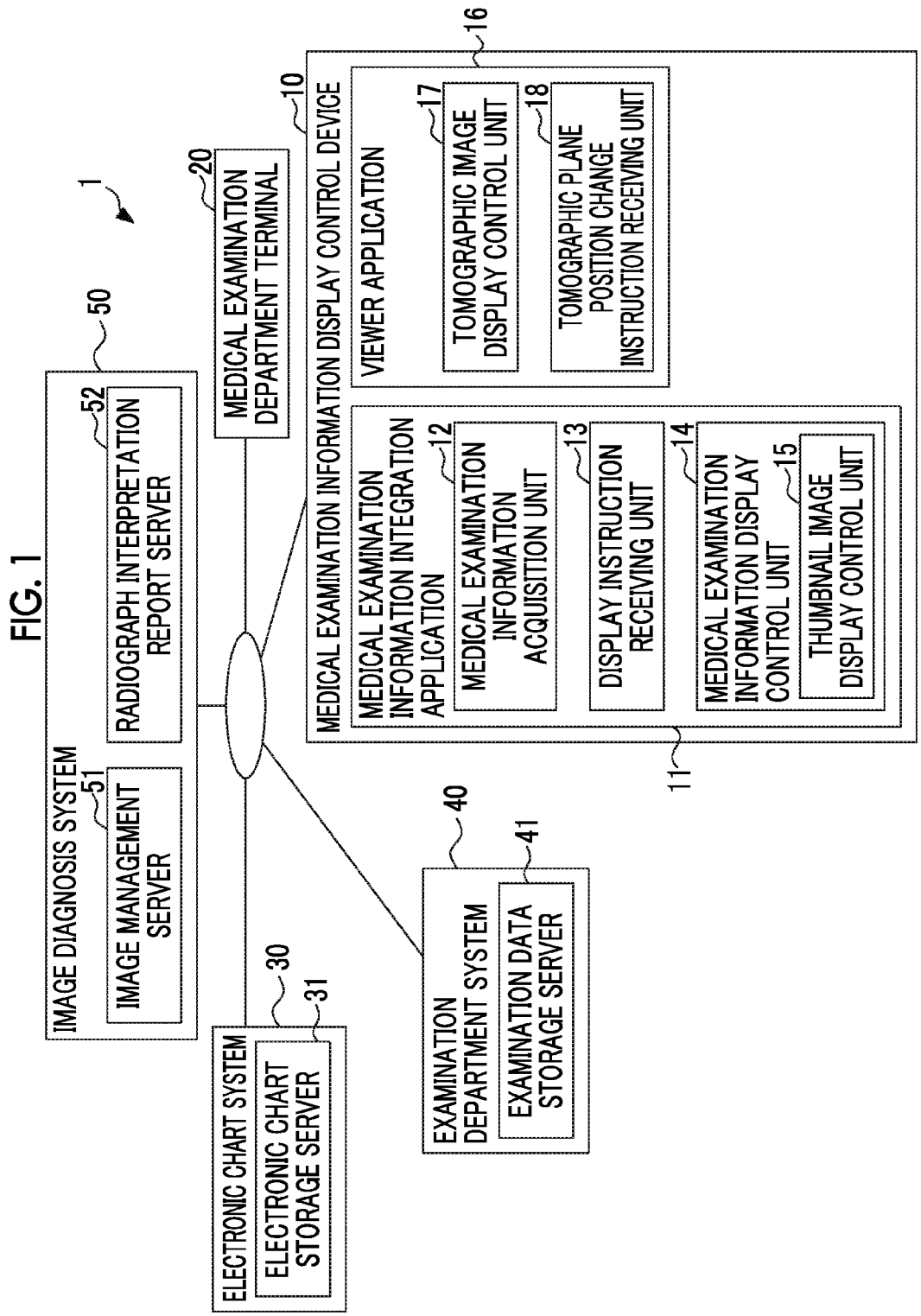
FIG. 1 is a block diagram schematically illustrating the structure of a medical examination information display system using an embodiment of an image display control device, a method for operating the image display control device, and an image display control program of the invention.

Hereinafter, a medical examination information display system using an embodiment of an image display control device, a method for operating the image display control device, and an image display control program according to the invention will be described in detail with reference to the drawings. FIG. 1 is a block diagram schematically illustrating the structure of a medical examination information display system 1 according to this embodiment.

As illustrated in FIG. 1, the medical examination information display system 1 according to this embodiment includes a medical examination information display control device 10, a medical examination department terminal 20, an electronic chart system 30, an examination department system 40, and an image diagnosis system 50.

First, the medical examination information display control device 10 will be described. The medical examination information display control device 10 includes an embodiment of the image display control device according to the invention.

The medical examination information display control device 10 includes a medical examination information integration application 11 that receives the identification information of a patient which is input from the medical examination department terminal 20, collects medical examination information related to the patient from the electronic chart system 30, the examination department system 40, and the image diagnosis system 50, integrates the collected information to generate a medical examination information display screen, and displays the medical examination information display screen on the medical examination department terminal 20 and a viewer application 16 that displays the image diagnosis information of the patient selected from the medical examination information display screen on an image display screen which is different from the medical examination information display screen. These applications are installed in a computer. The medical examination information integration application 11 and the viewer application 16 correspond to the medical examination information display control program according to this embodiment.

The medical examination information integration application 11 and the viewer application 16 may be different applications and may be recorded on a recording medium such as a CD-ROM. Alternatively, the medical examination information integration application 11 and the viewer application 16 may be downloaded from, for example, a server through the Internet, or may be provided by software as a service (SaaS) through the Internet.

A central processing unit (CPU) of the computer executes the medical examination information integration application 11 to implement the functions of a medical examination information acquisition unit 12, a display instruction receiving unit 13, a medical examination information display control unit 14, and a thumbnail image display control unit 15 illustrated in FIG. 1.

In addition, the central processing unit (CPU) of the computer executes the viewer application 16 to implement the functions of a tomographic image display control unit 17 and a tomographic plane position change instruction receiving unit 18 illustrated in FIG. 1.

The medical examination information acquisition unit 12 acquires the medical examination information associated with the identification information of the patient from each server, on the basis of the identification information of the patient input from the medical examination department terminal 20. Examples of the medical examination information include basic information, such as the name, age, and sex of the patient, various kinds of examination data, such as subject examination data and vital data, a radiograph interpretation report written by, for example, a doctor, and image information about the three-dimensional image of the subject.

The medical examination information display control unit 14 analyzes the medical examination information of the patient acquired by the medical examination information acquisition unit 12, generates a medical examination information display screen indicating the content of the medical examination information, and displays the medical examination information display screen on a monitor of the medical examination department terminal 20.

Figure 2:
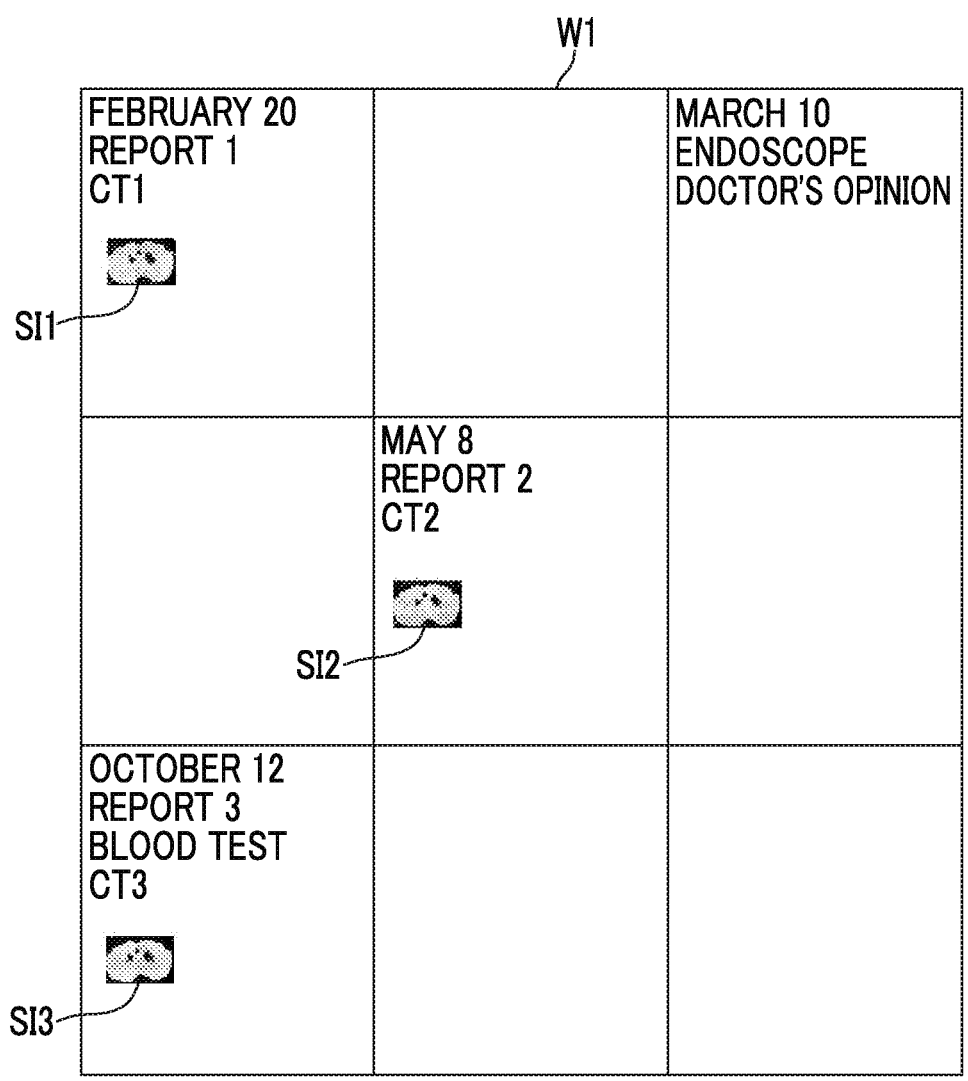
FIG. 2 is a diagram illustrating an example of a medical examination information display screen displayed by a medical examination information integration application.

FIG. 2 is a diagram illustrating an example of a medical examination information display screen W1 displayed by the medical examination information display control unit 14. In FIG. 2, the basic information of the patient is not illustrated. As illustrated in FIG. 2, a list of the names of the recorded medical examination information items of a certain patient is displayed on the medical examination information display screen W1 so as to be associated with a date.

Specifically, a radiograph interpretation report with a name "report 1" and a CT image with a name "CT1" are recorded on February 20 and a list of the names is displayed in the field of February 20. In addition, a radiograph interpretation report with a name "doctor's opinion" and an endoscopic image with a name "endoscope" are registered on March 10. A list of the names is displayed in the field of March 10. A radiograph interpretation report with a name "report 2" and a CT image with a name "CT2" are registered on May 8. A list of the names is displayed in the field of May 8. In addition, a radiograph interpretation report with a name "report 3", blood test data with a name "blood test", and a CT image with a name "CT3" are registered on October 12. A list of the names is displayed in the field of October 12.

As illustrated in FIG. 2, when three-dimensional image information, such as CT image information including a plurality of tomographic images, is included in the medical examination information, the thumbnail image display control unit 15 generates the thumbnail images of the tomographic images forming the three-dimensional image and the thumbnail images are displayed in each date field of the medical examination information display screen W1. In FIG. 2, since the CT image information is included in the fields of February 20, May 8, and October 12, thumbnail images SI1 to SI3 are displayed. The user, such as a doctor, observes the thumbnail images SI1 to SI3 to recognize the outline of the registered CT image information.

Each of the names is displayed on the medical examination information display screen W1 such that the user can select each name using an input device of the medical examination department terminal 20.

When the user selects each name, the display instruction receiving unit 13 receives the selected information as display instruction information. Information about a link to the medical examination information acquisition unit 12 is added to each name which is displayed on the medical examination information display screen W1. When the display instruction receiving unit 13 receives the display instruction information of each name, the medical examination information display control unit 14 reads the detailed medical examination information of the name from the medical examination information acquisition unit 12, with reference to the link destination added to the name, and displays the medical examination information on the monitor of the medical examination department terminal 20.

Specifically, for example, when the user clicks and selects "report 1" recorded on February 20, the medical examination information display control unit 14 reads the detailed content of "report 1" from the medical examination information acquisition unit 12 and displays the content on the monitor of the medical examination department terminal. When the user clicks and selects "CT1" recorded on February 20, the medical examination information display control unit 14 reads the detailed CT image of "CT1" from the medical examination information acquisition unit 12 and displays the CT image on the monitor of the medical examination department terminal. When the user clicks and selects "blood test" recorded on October 12, the medical examination information display control unit 14 reads the detailed examination data of "blood test" from the medical examination information acquisition unit 12 and displays the examination data on the monitor of the medical examination department terminal.

In this embodiment, when the user selects the name of image information on the medical examination information display screen W1 and the display instruction receiving unit 13 receives the selected information, the viewer application 16 starts.

Then, the image information read by the medical examination information display control unit 14 is output to the viewer application 16. The viewer application 16 displays the input image information on the monitor of the medical examination department terminal 20. At that time, the image information is displayed on an image display screen which is different from the medical examination information display screen. In this embodiment, the description is focused on a case in which a plurality of tomographic images forming a CT image are displayed on the image display screen.

As described above, the viewer application 16 includes the tomographic image display control unit 17 and the tomographic plane position change instruction receiving unit 18.

Figure 3:
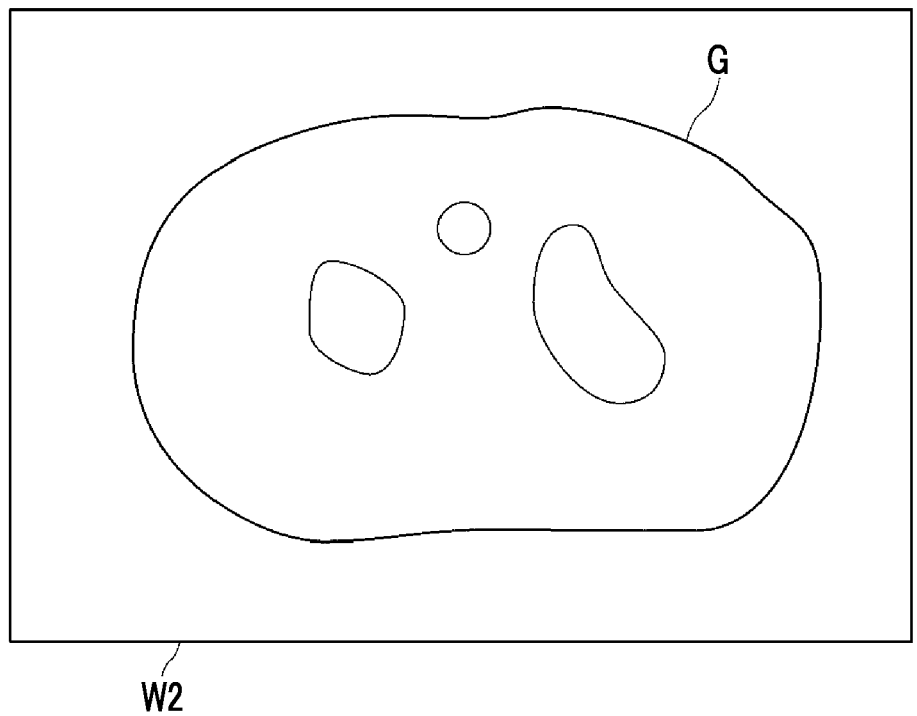
FIG. 3 is a diagram illustrating an example of an image display screen displayed by a viewer application.

When the user selects the name of a CT image on the medical examination information display screen W1, the tomographic image display control unit 17 acquires the CT image which is output from the medical examination information display control unit 14. The tomographic image display control unit 17 displays each tomographic image forming the input CT image on the image display screen. FIG. 3 illustrates an example of an image display screen W2. A predetermined tomographic image G is displayed on the image display screen W2 illustrated in FIG. 3.

Then, the tomographic plane position change instruction receiving unit 18 receives an instruction to change the position of the tomographic plane of the tomographic image displayed on the image display screen W2. Specifically, when the user inputs an instruction to change the position of the tomographic plane using the input device of the medical examination department terminal 20, the tomographic plane position change instruction receiving unit 18 receives the tomographic plane position change instruction.

When the tomographic plane position change instruction receiving unit 18 receives the tomographic plane position change instruction, the tomographic image display control unit 17 sequentially changes the tomographic image displayed on the image display screen W2 and displays the tomographic image, in response to the change instruction. The tomographic plane position change instruction may be an instruction to designate the detailed position of the tomographic plane or an instruction to change the position of the tomographic plane in an overlap order.

When the observation of the tomographic image by the user ends and an end instruction is input from the viewer application 16 to the input device of the medical examination department terminal 20, the tomographic image display control unit 17 ends the display of the tomographic image and outputs the information of the tomographic image which has been displayed immediately before the display of the tomographic image ends to the thumbnail image display control unit 15 of the medical examination information integration application 11. The information of the tomographic image may be the tomographic image which has been displayed immediately before the viewer application 16 ends or information indicating the position of the tomographic plane of the tomographic image.

As described above, when the information of the tomographic image displayed immediately before the viewer application 16 ends is input, the thumbnail image display control unit 15 newly generates a thumbnail image of the tomographic image, changes the thumbnail image which is currently being displayed to the newly generated thumbnail image, and displays the newly generated thumbnail image. That is, the thumbnail image display control unit 15 changes thumbnail images SI1 to SI3 illustrated in FIG. 2 to the thumbnail images of the tomographic images displayed immediately before the viewer application 16 ends. The medical examination information display control device 10 has been described above.

Next, as described above, the medical examination department terminal 20 includes: a display which displays the medical examination information display screen W1 illustrated in FIG. 2 and the image display screen W2 illustrated in FIG. 3; and an input device which includes, for example, a keyboard and a mouse and receives the input identification information of the patient, an input instruction to display (select) medical examination information, an input instruction to change the position of the tomographic plane of the tomographic image, an input instruction to start the medical examination information integration application 11, and an input instruction to end the viewer application 16.

The electronic chart system 30 manages the electronic charts of a plurality of patients. The electronic chart system 30 includes an electronic chart storage server 31. The electronic chart storage server 31 stores the electronic charts of a plurality of patients so as to be associated with the identification information of the patients. The electronic chart system 30 acquires the identification information of the patient input by the medical examination department terminal 20 and outputs information about the electronic chart associated with the identification information to the medical examination information display control device 10. The electronic chart includes the basic information of the patient, information about the kind of medicine or medicinal drops, a dosing period, and an anamnesis, and data for the doctor's medical interview.

The examination department system 40 manages the examination data of a plurality of patients. The examination department system 40 includes an examination data storage server 41. The examination data storage server 41 stores the examination data of a plurality of patients so as to be associated with the identification information of the patients. The examination department system 40 acquires the identification information of the patient input from the medical examination department terminal 20 and outputs the examination data associated with the identification information to the medical examination information display control device 10.

The image diagnosis system 50 manages the image medical examination information of a plurality of patients. The image diagnosis system 50 includes an image management server 51 and a radiograph interpretation report server 52. The image management server 51 stores image information, such as the three-dimensional images of a plurality of patients, so as to be associated with the identification information of the patients. The radiograph interpretation report server 52 stores a radiograph interpretation report written by the doctor who has observed, for example, a radiological image. The radiograph interpretation report is stored so as to be associated with, for example, the radiological image stored in the image management server 51.

The image diagnosis system 50 acquires the identification information of the patient input from the medical examination department terminal 20 and outputs the three-dimensional image associated with the identification information or the radiograph interpretation report on the three-dimensional image to the medical examination information display control device 10.

Figure 4:
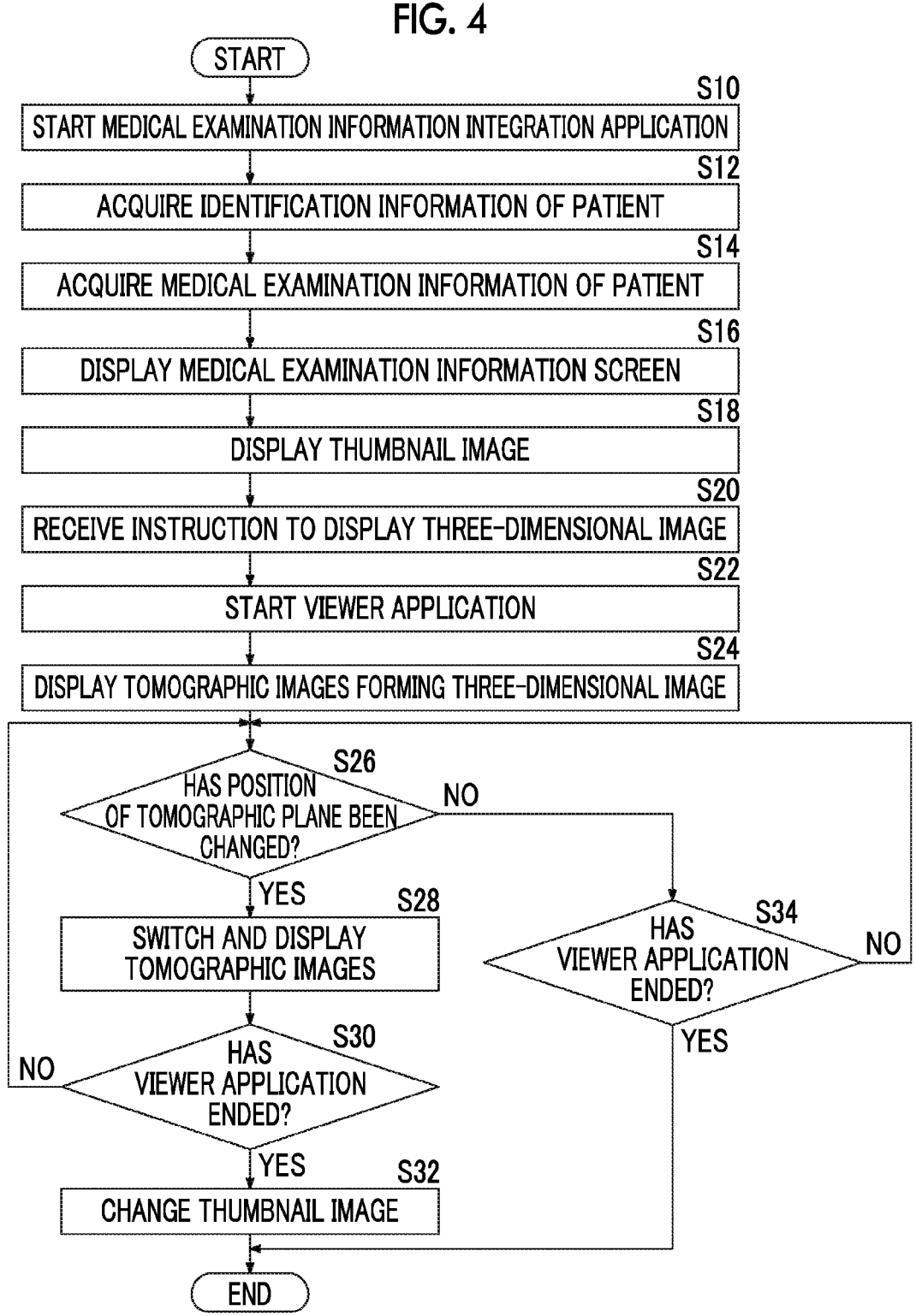
FIG. 4 is a flowchart illustrating the operation of the medical examination information display system using an embodiment of the image display control device, the method for operating the image display control device, and the image display control program of the invention.

Next, the operation of the medical examination information display system 1 according to this embodiment will be described with reference to a flowchart illustrated in FIG. 4. The medical examination information display system 1 according to this embodiment is characterized in that the thumbnail image of the tomographic image on the medical examination information display screen W1 is changed. Therefore, the following description is focused on the change in the thumbnail image.

First, the medical examination department terminal 20 inputs an instruction to start the medical examination information integration application 11 and the medical examination information integration application 11 starts in response to the input instruction (S10).

Then, the identification information of the patient is input and the medical examination information acquisition unit 12 of the medical examination information display control device 10 acquires the identification information of the patient (S12).

The medical examination information acquisition unit 12 collects the medical examination information related to the patient from the electronic chart storage server 31, the examination data storage server 41, the image management server 51, and the radiograph interpretation report server 52, on the basis of the input identification information of the patient, and temporarily stores the medical examination information (S14).

Then, the medical examination information display control unit 14 analyzes the medical examination information stored in the medical examination information acquisition unit 12, generates the medical examination information display screen W1 indicating the content of the medical examination information, and displays the medical examination information display screen W1 on the monitor of the medical examination department terminal 20 (S16). In this case, when a three-dimensional image is included in the medical examination information, the thumbnail image display control unit 15 generates the thumbnail image of a predetermined tomographic image forming the three-dimensional image and displays the thumbnail image on the medical examination information display screen W1 (S18).

In this embodiment, for example, it is assumed that the thumbnail image of the tomographic image at the position of the tomographic plane closest to the end is displayed on the initial medical examination information display screen W1. Specifically, for example, when the tomographic images forming the three-dimensional image are the axial tomographic images of the chest, the thumbnail image of the tomographic image that is closest to the head is displayed. However, the invention is not limited thereto. The user can arbitrarily set the position of the tomographic plane of the thumbnail image displayed on the initial medical examination information display screen W1.

Then, when the user selects the name of three-dimensional image information on the medical examination information display screen W1 and inputs an instruction to display the three-dimensional image information, the display instruction receiving unit 13 receives the display instruction (S20) and the viewer application 16 starts in response to the display instruction (S22).

Then, the medical examination information display control unit 14 reads the three-dimensional image selected by the user from the medical examination information acquisition unit 12 and outputs the three-dimensional image to the viewer application 16. The tomographic image display control unit 17 of the viewer application 16 displays a predetermined tomographic image among a plurality of tomographic images forming the input three-dimensional image on the image display screen W2 displayed on the monitor of the medical examination department terminal 20 (S24). In this case, the displayed tomographic image is a tomographic image before reduction which is arranged in the same tomographic plane as the thumbnail image displayed on the medical examination information display screen W1.

Then, when the user inputs an instruction to change the position of the tomographic plane of the tomographic image displayed on the image display screen W2 (S26, YES), the tomographic plane position change instruction receiving unit 18 receives the change instruction and the tomographic image display control unit 17 switches the tomographic image displayed on the image display screen W2 in response to the change instruction and displays the tomographic image (S28).

Then, when the user ends the switching of the tomographic image and the observation of the tomographic image and inputs an instruction to end the viewer application 16, the image display screen W2 is closed and the viewer application 16 ends (S30, YES). Then, in this case, the information of the tomographic image displayed immediately before the viewer application 16 ends is input to the thumbnail image display control unit 15 of the medical examination information integration application 11. The thumbnail image display control unit 15 newly generates a thumbnail image on the basis of the input information of the tomographic image, changes the thumbnail image that is currently being displayed on the medical examination information display screen W1 to the newly generated thumbnail image, and displays the newly generated thumbnail image (S32).

When the user inputs an instruction to end the viewer application, without inputting an instruction to change the position of the tomographic plane of the tomographic image displayed on the image display screen W2 (S26: NO, S34: YES), the process of changing the thumbnail image is not performed.

According to the medical examination information display system of the above-described embodiment, when the display of the tomographic image by the viewer application 16 ends, a thumbnail image of the tomographic image displayed immediately before the end of the display is newly generated. Then, the thumbnail image that is currently being displayed on the medical examination information display screen is changed to the newly generated thumbnail image and the newly generated thumbnail image is displayed. Therefore, when observing the changed and displayed thumbnail image, the user can instantaneously check which of the tomographic images has been mainly observed in the previous radiograph interpretation. Therefore, it is possible to improve the efficiency of diagnosis.

In the above-described embodiment, the user selects one of the names of a plurality of three-dimensional images displayed on the medical examination information display screen W1. However, the invention is not limited thereto. The system may be configured such that the user can select the names of a plurality of three-dimensional images. Specifically, for example, the system may be configured such that "CT1", "CT2", and "CT3" which are the names of three-dimensional images, can be simultaneously selected on the medical examination information display screen W1 illustrated in FIG. 5. As a method for selecting them at the same time, for example, a method may be used in which the user clicks the names of the three-dimensional images with the mouse while pressing a predetermined key of the keyboard in the medical examination department terminal 20, thereby selecting the names at the same time. When the user selects the names and presses an enter key, the viewer application 16 starts.

As described above, when the names of a plurality of three-dimensional images are selected, the tomographic image display control unit 17 may display the tomographic images of the three-dimensional images side by side on the image display screen W2 as illustrated in FIG. 5. As such, since the tomographic images of a plurality of three-dimensional images are displayed side by side, it is possible to easily perform comparative radiograph interpretation.

For the layout of the tomographic images of a plurality of three-dimensional images, for example, when two tomographic images are displayed side by side, they may be displayed in a 1×2 layout. When three tomographic images are displayed side by side, they may be displayed in a 1×3 layout. When four tomographic images are displayed side by side, they may be displayed in a 2×2 layout.

As described above, when the tomographic images of a plurality of three-dimensional images are displayed side by side, it is preferable that the tomographic image display control unit 17 switches the plurality of tomographic images in operative association with each other so as to be located in the same tomographic plane and displays the tomographic images. As a method for switching a plurality of tomographic images in operative association with each other and displaying the tomographic images as described above, for example, a method may be used which manually aligns the positions of the tomographic planes of the plurality of tomographic images first, switches the plurality of tomographic images in operative association with each other at the interval between the tomographic planes which is set in DICOM in advance, and displays the tomographic images.

Figure 6:
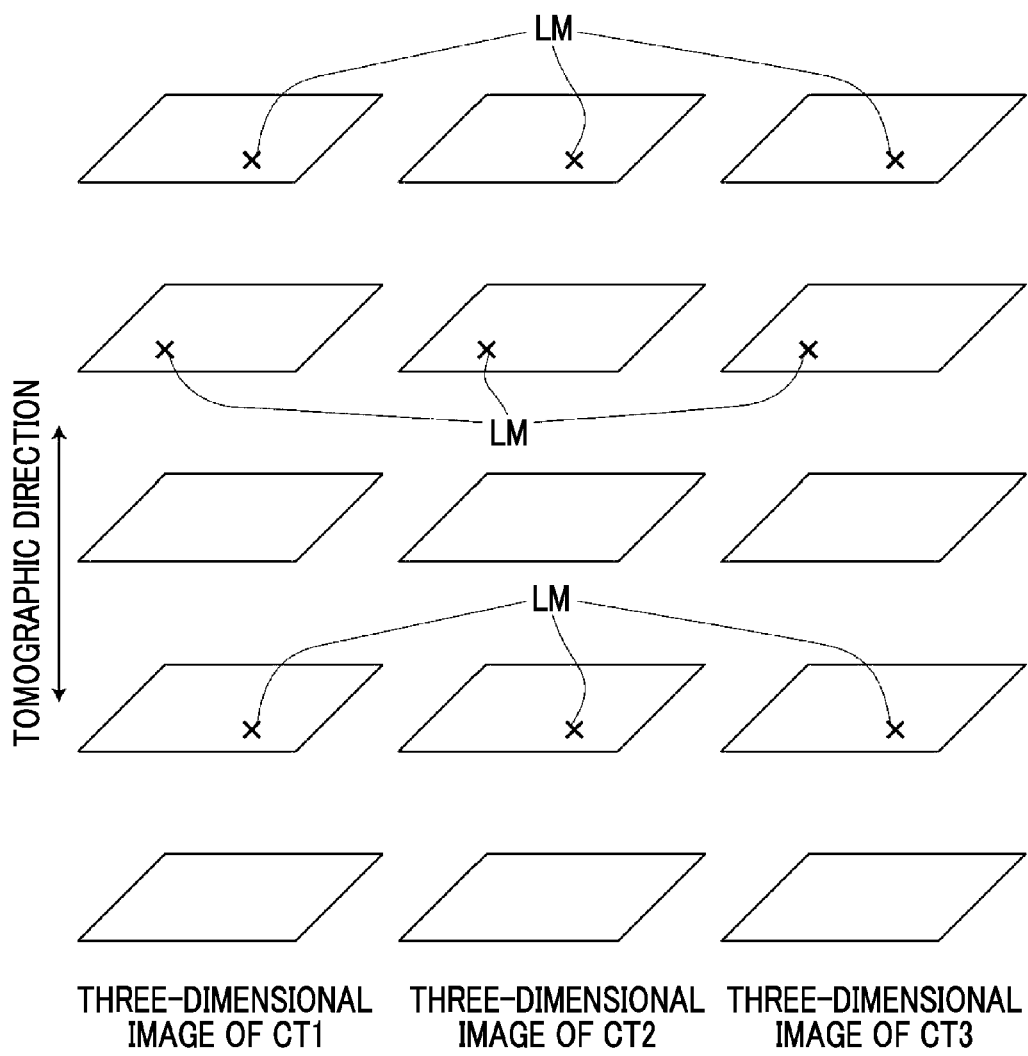
FIG. 6 is a diagram illustrating a case in which the tomographic images of each three-dimensional image are displayed such that the positions of the tomographic planes of the tomographic images are operatively associated with each other, on the basis of a landmark detected from a plurality of three-dimensional images.

Alternatively, a method may be used which automatically detects a landmark, such as an anatomic feature point, from a plurality of tomographic images forming three-dimensional images and displays each tomographic image at the position of the common landmark LM detected from a plurality of three-dimensional images, as illustrated in FIG. 6, thereby switching the positions of the tomographic planes of a plurality of tomographic images so as to be operatively associated with each other. In addition, for example, the apex of the lung, a rib, or a center point of the organ, such as the liver, can be used as the landmark LM. However, the invention is not limited thereto. Other landmarks may be detected. A known method can be used to detect the landmark LM.

As described above, when the tomographic images of a plurality of three-dimensional images are displayed side by side and the imaging directions of the plurality of three-dimensional images are different from each other, it is preferable that the tomographic images having the same imaging direction are reconstructed and displayed side by side. Specifically, for example, when the imaging direction of one three-dimensional image is an axial direction and the imaging direction of the other three-dimensional image is a sagittal direction, the tomographic images captured in the sagittal direction may be reconstructed using the three-dimensional image captured in the axial direction and two tomographic images captured in the sagittal direction may be displayed side by side. Information about the imaging direction of the three-dimensional image is set in, for example, DICOM in advance. In addition, for example, the method disclosed in JP2011-120827A can be used to generate the tomographic images having the same imaging direction.

Figure 7:
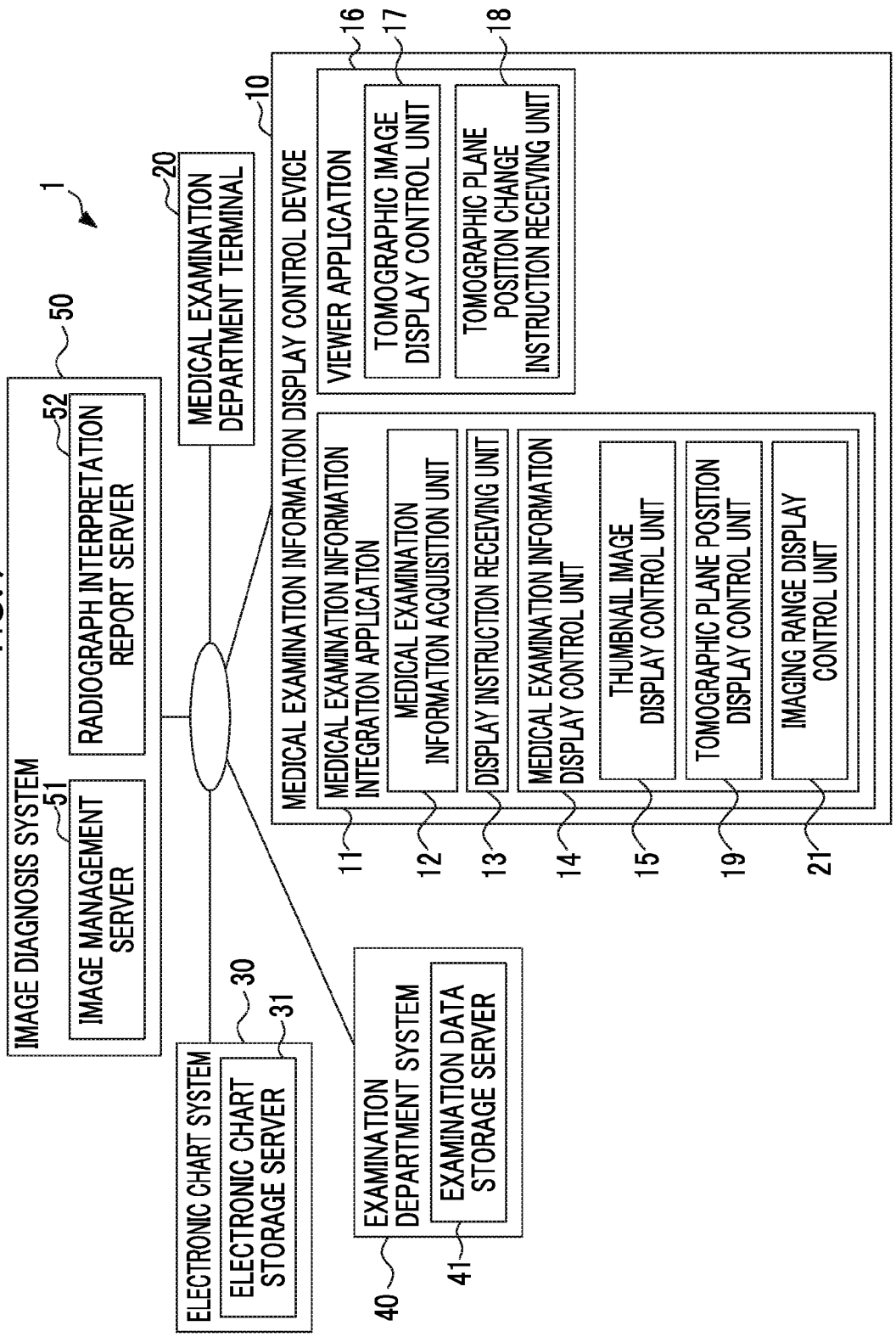
FIG. 7 is a block diagram illustrating a modification example of the medical examination information display system illustrated in FIG. 1.
Figure 8:
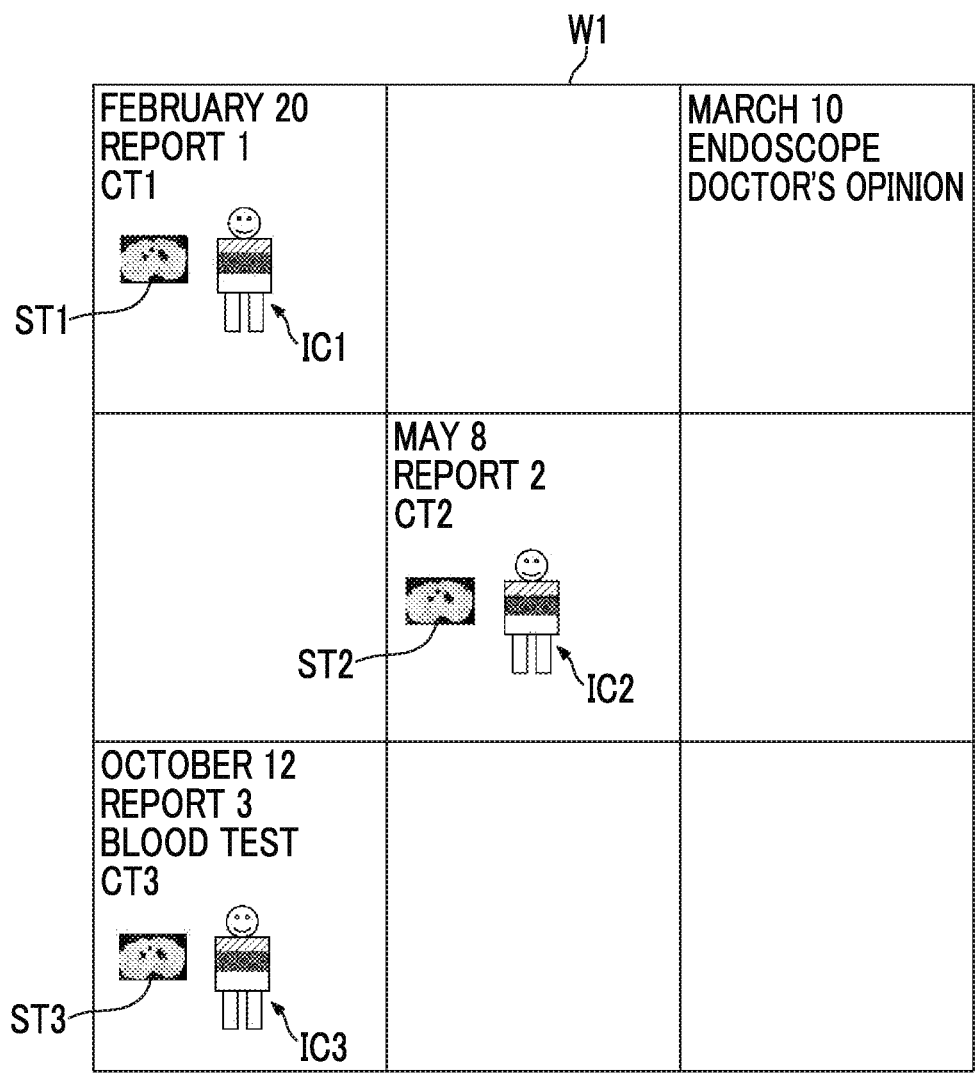
FIG. 8 is a diagram illustrating an example of a medical examination information display screen on which the position of a tomographic plane of a thumbnail image and an imaging range are displayed on an icon.

As illustrated in FIG. 7, a tomographic plane position display control unit 19 and an imaging range display control unit 21 may be further provided. As illustrated in FIG. 8, body icons IC1 to IC3 may be further displayed in the fields in which the names of three-dimensional image information are written on the medical examination information display screen W1. The tomographic plane position display control unit 19 may display an image indicating the position of the tomographic plane on the icons IC1 to IC3 and the imaging range display control unit 21 may display an image indicating the imaging range on the icons IC1 to IC3.

Here, the position of the tomographic plane displayed by the tomographic plane position display control unit 19 indicates the position of the tomographic plane of the thumbnail image, which is currently being displayed on the medical examination information display screen W1, in the human body. Therefore, for example, when the viewer application 16 changes the position of the tomographic plane of the tomographic image such that the thumbnail image displayed on the medical examination information display screen W1 is changed to a new thumbnail image, the position of the tomographic plane of the new thumbnail image is displayed on the body icon.

The imaging range displayed by the imaging range display control unit 21 is, for example, an imaging range when a three-dimensional image is captured. For example, the imaging range is the range of the chest or the abdomen. Information about the imaging range is set in, for example, DICOM in advance.

Next, an example of the display of the icon will be described with reference to FIGS. 9 to 11.

Figure 9:
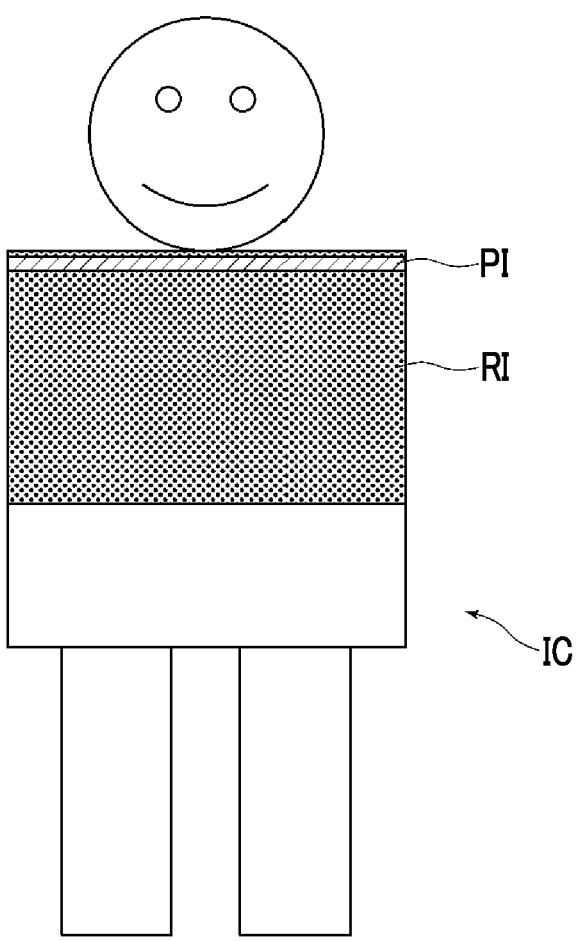
FIG. 9 is a diagram illustrating an example of an icon when the imaging range of a three-dimensional image is the chest and the imaging direction thereof is an axial direction.

FIG. 9 illustrates an icon IC which is displayed on the initial medical examination information display screen W1 when the imaging range of the three-dimensional image is the chest and the imaging direction is the axial direction. When the imaging range of the three-dimensional image is the chest and the imaging direction is the axial direction, the thumbnail image of the tomographic image that is closest to the head is displayed on the initial medical examination information display screen W1, as described above. Therefore, an image PI indicating the position of the tomographic plane that is closest to the head is displayed on the icon IC. In addition, an image RI indicating the imaging range of the chest is displayed on the icon IC.

Figure 10:
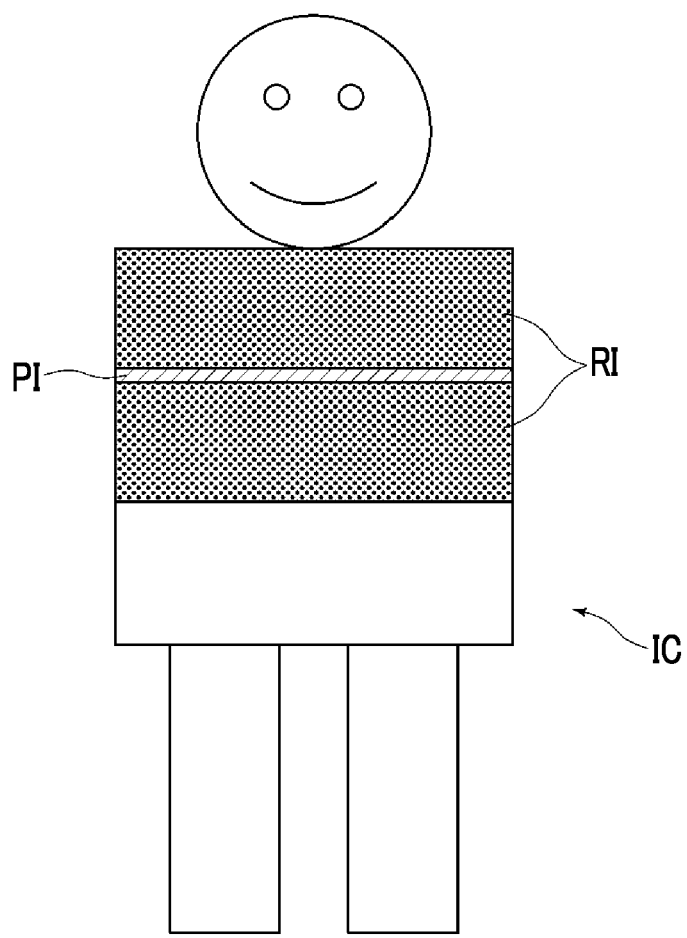
FIG. 10 is a diagram illustrating an example of an icon when the imaging range of a three-dimensional image is the chest and the imaging direction thereof is the axial direction.

FIG. 10 illustrates an icon IC when the viewer application 16 changes the position of the tomographic plane of the tomographic image on the medical examination information display screen W1 on which the icon IC illustrated in FIG. 9 is displayed to change the thumbnail image displayed on the medical examination information display screen W1. In the icon IC illustrated in FIG. 10, the image PI indicating the position of the tomographic plane is located at the enter of the chest. Therefore, it is possible to instantaneously recognize that the position of the tomographic plane of the tomographic image observed by the user immediately before the viewer application 16 ends is the center of the chest and the position of the tomographic plane of the thumbnail image which is currently being displayed is the center of the chest.

Figure 11:
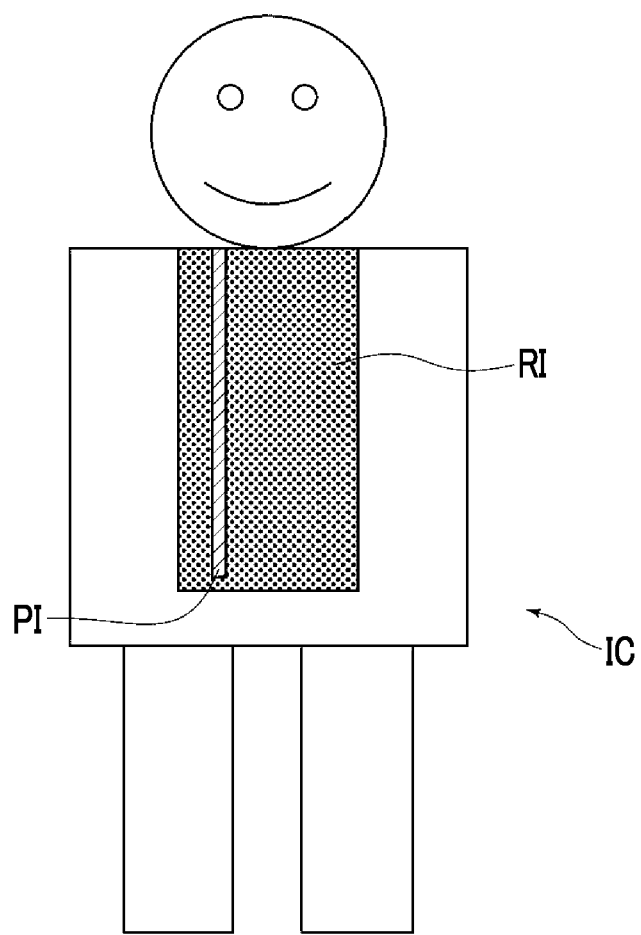
FIG. 11 is a diagram illustrating an example of an icon when the imaging range of a three-dimensional image is the chest and the imaging direction thereof is a sagittal direction.
Figure 12:
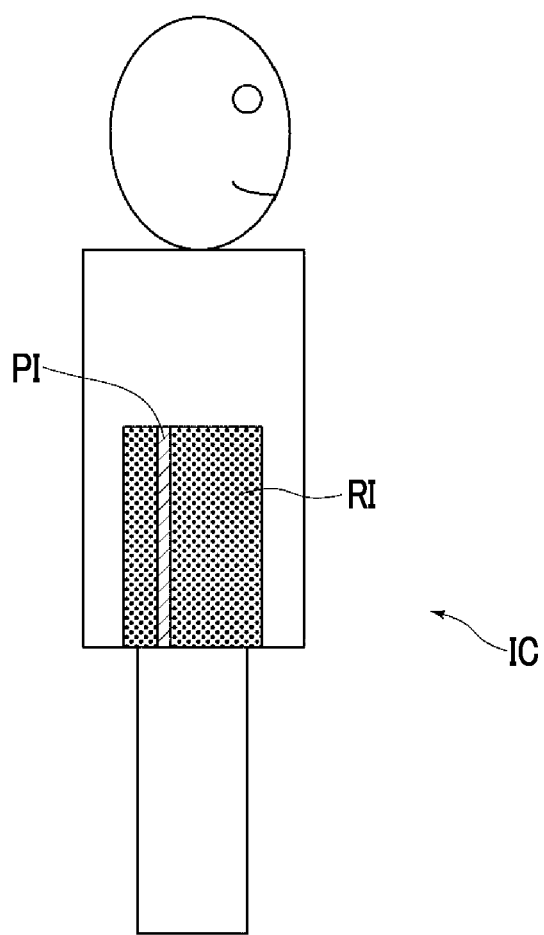
FIG. 12 is a diagram illustrating an example of an icon when the imaging range of a three-dimensional image is the abdomen and the imaging direction thereof is a coronal direction.

FIG. 11 illustrates an icon IC when the imaging range of the three-dimensional image is the chest and the imaging direction is a sagittal direction. FIG. 12 illustrates an icon IC when the imaging range of the three-dimensional image is the abdomen and the imaging direction is a coronal direction. In FIG. 11, the image RI indicating the imaging range of the chest and the image PI indicating the position of the tomographic plane of the thumbnail image in the chest are displayed on the icon IC. In FIG. 12, the image RI indicating the imaging range of the abdomen and the image PI indicating the position of the tomographic plane of the thumbnail image in the abdomen are displayed on the icon IC.

The example of the display of the icon is not limited to the above. Icons having any other shapes may be displayed as long as they enable the user to recognize the imaging range of the three-dimensional image in the human body and the position of the tomographic plane of the thumbnail image.

What is claimed is:

1. An image display control device comprising:
    a thumbnail image display control unit that displays a thumbnail image of a tomographic image forming a three-dimensional image including a plurality of tomographic images;
    a display instruction receiving unit that receives an instruction to display the three-dimensional image; and
    a tomographic image display control unit that displays the plurality of tomographic images forming the three-dimensional image on a display screen which is different from a display screen on which the thumbnail image is displayed such that the tomographic images are sequentially switchable, when the display instruction receiving unit receives the instruction to display the three-dimensional image,
    wherein the thumbnail image display control unit newly generates a thumbnail image of the tomographic image displayed by the tomographic image display control unit immediately before the display of the tomographic image ends, changes the thumbnail image that is currently being displayed to the newly generated thumbnail image, and displays the newly generated thumbnail image.

2. The image display control device according to claim 1, wherein the display instruction receiving unit receives an instruction to display a plurality of three-dimensional images to be displayed among a plurality of three-dimensional images, and
    when the display instruction receiving unit receives the instruction to display the plurality of three-dimensional images to be displayed, the tomographic image display control unit displays the tomographic images of the plurality of three-dimensional images to be displayed side by side.

3. The image display control device according to claim 2, wherein the tomographic image display control unit switches the plurality of tomographic images displayed side by side in operative association with each other such that a plurality of tomographic images located in the same tomographic plane are displayed side by side and displays the plurality of tomographic images.

4. The image display control device according to claim 3, wherein the tomographic image display control unit switches the plurality of tomographic images in operative association with each other, on the basis of a landmark which is detected in advance from each of the plurality of three-dimensional images to be displayed, and displays the plurality of tomographic images.

5. The image display control device according to claim 2, wherein, when the plurality of three-dimensional images to be displayed have different imaging directions, the tomographic image display control unit generates tomographic images having the same imaging direction and displays the tomographic images.

6. The image display control device according to claim 1, further comprising:
    a tomographic plane position change instruction receiving unit that receives an instruction to change the position of a tomographic plane of a tomographic image to be displayed among the plurality of tomographic images forming the three-dimensional image,
    wherein the tomographic image display control unit displays the tomographic image at the position of the tomographic plane changed by the tomographic plane position change instruction receiving unit.

7. The image display control device according to claim 1, further comprising:
    a tomographic plane position display control unit that displays an image indicating the position of a tomographic plane of the thumbnail image, which is currently being displayed, on a display screen on which the thumbnail image is displayed.

8. The image display control device according to claim 7, wherein the tomographic plane position display control unit displays the image indicating the position of the tomographic plane on a body icon.

9. The image display control device according to claim 1, further comprising:
    an imaging range display control unit that displays an image indicating an imaging range of a three-dimensional image including the thumbnail image, which is currently being displayed, on the display screen on which the thumbnail image is displayed.

10. The image display control device according to claim 9,
    wherein the imaging range display control unit displays the image indicating the imaging range on the body icon.

11. A method for operating an image display control device including a thumbnail image display control unit, a display instruction receiving unit, and a tomographic image display control unit, the method comprising:
    allowing the thumbnail image display control unit to display a thumbnail image of a tomographic image forming a three-dimensional image including a plurality of tomographic images;
    allowing the display instruction receiving unit to receive an instruction to display the three-dimensional image;
    allowing the tomographic image display control unit to display the plurality of tomographic images forming the three-dimensional image on a display screen which is different from a display screen on which the thumbnail image is displayed such that the tomographic images are sequentially switchable, when the instruction to display the three-dimensional image is received; and allowing the thumbnail image display control unit to newly generate a thumbnail image of the tomographic image displayed immediately before the display of the tomographic image ends, to change the thumbnail image that is currently being displayed to the newly generated thumbnail image, and to display the newly generated thumbnail image.

12. A non-transitory computer-readable recording medium having stored therein an image display control program that causes a computer to function as:
- a thumbnail image display control unit that displays a thumbnail image of a tomographic image forming a three-dimensional image including a plurality of tomographic images;
- a display instruction receiving unit that receives an instruction to display the three-dimensional image; and
- a tomographic image display control unit that displays the plurality of tomographic images forming the three-dimensional image on a display screen which is different from a display screen on which the thumbnail image is displayed such that the tomographic images are sequentially switchable, when the display instruction receiving unit receives the instruction to display the three-dimensional image, wherein the thumbnail image display control unit newly generates a thumbnail image of the tomographic image displayed by the tomographic image display control unit immediately before the display of the tomographic image ends, changes the thumbnail image that is currently being displayed to the newly generated thumbnail image, and displays the newly generated thumbnail image.

* * * * *